United States Patent
Kim et al.

(10) Patent No.: US 11,241,499 B2
(45) Date of Patent: Feb. 8, 2022

(54) HUMAN SERUM ALBUMIN IN FORMULATIONS

(71) Applicant: Regeneron Pharmaceuticals, Inc., Tarrytown, NY (US)

(72) Inventors: Dorothy Kim, Brooklyn, NY (US); Michael Marlow, Greenwich, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/807,406

(22) Filed: Mar. 3, 2020

(65) Prior Publication Data

US 2020/0282063 A1 Sep. 10, 2020

Related U.S. Application Data

(60) Provisional application No. 62/813,843, filed on Mar. 5, 2019.

(51) Int. Cl.
*A61K 47/42* (2017.01)
*A61K 47/26* (2006.01)

(52) U.S. Cl.
CPC ............. *A61K 47/42* (2013.01); *A61K 47/26* (2013.01)

(58) Field of Classification Search
CPC ...................................................... A61K 9/08
See application file for complete search history.

(56) References Cited

FOREIGN PATENT DOCUMENTS

WO WO 2017/117311 A1 7/2017

OTHER PUBLICATIONS

Rasmussen et al., Pharm Res., 2010, 27:1337-1347.*
Taneja et al., International J of Pharmaceutics, 2018, 536:82-94.*
Garidel P et al: "A thermodynamic analysis of the binding interaction between polysorbate 20 and 80 with human serum albumins and immunoglobulins: A contribution to understand colloidal protein stabilisation", Biophysical Chemistry, Elsevier, Amsterdam, NL, vol. 143, No. 1-2, Jul. 1, 2009, pp. 70-78.
Fabio Polticelli et al: "GA/GB Fold switching may modulate fatty acid transfer from human serum albumin to bacteria", IUBMB LIFE, vol. 64, No. 11, Oct. 22, 2012, pp. 885-888.
International Search Report PCT Application No. PCT/US2020/020752, International Filing Date Mar. 3, 2020, dated Jun. 19, 2020.

* cited by examiner

*Primary Examiner* — Bin Shen
(74) *Attorney, Agent, or Firm* — Kramer Levin Naftalis & Frankel LLP

(57) ABSTRACT

Drug formulations and methods for removing, reducing, or preventing the formation of fatty acid particles in drug formulations are provided.

10 Claims, 9 Drawing Sheets

HUMAN SERUM ALBUMIN IN FORMULATIONS

FIELD

The present invention generally pertains to methods for removing, reducing, or preventing the formation of fatty acid particles in drug formulations.

BACKGROUND

There are many challenges in designing drug formulations in order to improve their manufacturing, storage, handling, and administration characteristics while also minimizing unwanted side effects. For example, formulation development seeks to identify solution conditions and additives or excipients that increase the stability and reduce the occurrence of chemical or physical changes that often result in aggregation, and may subsequently lead to an increase in sub-visible or visible particles.

Preventing and reducing the formation of particles in formulated injectable drug products has been particularly challenging and the focus of debate and investigation within the pharmaceutical industry for several years. Consisting of synthetic or biological materials and originating from various sources, particles that are visible or even sub-visible can raise the potential for immunogenicity in patients and may have varying effects on the drug product quality. One such possible impurity could be fatty acid particles that are formed during manufacture, shipment, storage, handling or administration. The fatty acid particles could potentially cause adverse immunogenic effects and impact shelf life.

It will be appreciated that a need exists for improved methods to reduce or prevent the formation of fatty acid particles in protein formulations and for protein formulations that have reduced level of fatty acid particles.

SUMMARY

Maintaining stability of drug formulations, not only during storage but also during manufacturing, shipment, handling and administration, is a major challenge. Among drug products, protein biotherapeutics are gaining popularity due to their success and versatility. Therapeutic proteins are the fastest growing class of drugs and make up about one third of the drug market. One of the major challenges for protein biotherapeutics development is to overcome the limited stability of the proteins which can be affected by presence of visible and sub-visible particles. This is due to increasing concerns about the potential immunogenicity of particles-both proteinaceous particles and non-proteinaceous particles. Mitigation of the formation of such particles can be an important step in the drug formulation development. An example of one challenge is preventing or reducing formation of fatty acid particles in formulations.

The disclosure provides a method of preventing or reducing formation of fatty acid particles in a formulation.

In one exemplary embodiment, the method of preventing or reducing formation of fatty acid particles in a formulation can comprise adding human serum albumin to a formulation capable of forming fatty acid particles.

In one aspect of this embodiment, the method of preventing or reducing formation of fatty acid particles in a formulation can comprise adding human serum albumin in an effective amount to a formulation capable of forming fatty acid particles.

In one aspect of this embodiment, the method of preventing or reducing formation of fatty acid particles in a formulation can comprise adding human serum albumin to a formulation capable of forming fatty acid particles, wherein the formulation capable of forming fatty acid particles can comprise polysorbate.

In one aspect of this embodiment, the method of preventing or reducing formation of fatty acid particles in a formulation can comprise adding human serum albumin to a formulation capable of forming fatty acid particles, wherein the formulation capable of forming fatty acid particles comprises polysorbate selected from the group consisting of polysorbate 20, polysorbate 40, polysorbate 60, polysorbate 80, and combinations thereof.

In one aspect of this embodiment, the method of preventing or reducing formation of fatty acid particles in a formulation can comprise adding human serum albumin to a formulation capable of forming fatty acid particles, wherein the formulation capable of forming fatty acid particles comprises about 0.001% w/v to about 1% w/v of polysorbate.

In one aspect of this embodiment, the method of preventing or reducing formation of fatty acid particles in a formulation can comprise adding human serum albumin to a formulation capable of forming fatty acid particles, wherein the formulation capable of forming fatty acid particles comprises polysorbate and at least one protein.

In one aspect of this embodiment, the method of preventing or reducing formation of fatty acid particles in a formulation can comprise adding human serum albumin to a formulation capable of forming fatty acid particles, wherein the formulation capable of forming fatty acid particles comprises polysorbate and an antibody.

In one aspect of this embodiment, the method of preventing or reducing formation of fatty acid particles in a formulation can comprise adding human serum albumin to a formulation capable of forming fatty acid particles, wherein the fatty acid particles comprises free fatty acids.

In one aspect of this embodiment, the method of preventing or reducing formation of fatty acid particles in a formulation can comprise adding human serum albumin to a formulation capable of forming fatty acid particles, wherein the fatty acid particles comprise free fatty acids and wherein a ratio of molecules of free fatty acid to molecules of human serum albumin can be about 6:1 to about 1:1.

In one aspect of this embodiment, the method of preventing or reducing formation of fatty acid particles in a formulation can comprise adding human serum albumin to a formulation capable of forming fatty acid particles, wherein the fatty acid particles comprises free fatty acids selected from the group consisting of oleic acid, palmitic acid, stearic acid, myristic acid, lauric acid, and combinations thereof.

In one aspect of this embodiment, the method of preventing or reducing formation of fatty acid particles in a formulation can comprise adding human serum albumin to a formulation capable of forming fatty acid particles, wherein the formulation can comprise at least about 5.5 mg/mL human serum albumin.

In one aspect of this embodiment, the method of preventing or reducing formation of fatty acid particles in a formulation can comprise adding human serum albumin to a formulation capable of forming fatty acid particles, wherein the formulation can be a parenteral formulation.

In one aspect of this embodiment, the method of preventing or reducing formation of fatty acid particles in a formulation can comprise adding human serum albumin to a formulation capable of forming fatty acid particles, wherein the fatty acid particles are visible or sub-visible particles.

In one aspect of this embodiment, the method of preventing or reducing formation of fatty acid particles in a formulation can comprise adding human serum albumin to a formulation capable of forming fatty acid particles, wherein the fatty acid particles can be detectable by Raman spectroscopy.

The disclosure, at least in part, provides a method of solubilizing fatty acid particles in a formulation.

In one exemplary embodiment, the method of solubilizing fatty acid particles in a formulation can comprise adding human serum albumin to a formulation capable of forming fatty acid particles.

In one aspect of this embodiment, the method of solubilizing fatty acid particles in a formulation can comprise adding an effective amount of human serum albumin to a formulation capable of forming fatty acid particles.

In one aspect of this embodiment, the method of solubilizing fatty acid particles in a formulation can comprise adding human serum albumin to a formulation capable of forming fatty acid particles, wherein the formulation capable of forming fatty acid particles can comprise polysorbate.

In one aspect of this embodiment, the method of solubilizing fatty acid particles in a formulation can comprise adding human serum albumin to a formulation capable of forming fatty acid particles, wherein the formulation capable of forming fatty acid particles can comprise polysorbate selected from the group consisting of polysorbate 20, polysorbate 40, polysorbate 60, polysorbate 80, and combinations thereof.

In one aspect of this embodiment, the method of solubilizing fatty acid particles in a formulation can comprise adding human serum albumin to a formulation capable of forming fatty acid particles, wherein the formulation capable of forming fatty acid particles can comprise about 0.001% w/v to about 1% w/v of polysorbate.

In one aspect of this embodiment, the method of solubilizing fatty acid particles in a formulation can comprise adding human serum albumin to a formulation capable of forming fatty acid particles, wherein the formulation capable of forming fatty acid particles can comprise polysorbate and at least one protein.

In one aspect of this embodiment, the method of solubilizing fatty acid particles in a formulation can comprise adding human serum albumin to a formulation capable of forming fatty acid particles, wherein the formulation capable of forming fatty acid particles comprises polysorbate and an antibody.

In one aspect of this embodiment, the method of solubilizing fatty acid particles in a formulation can comprise adding human serum albumin to a formulation capable of forming fatty acid particles, wherein the fatty acid particles can comprise free fatty acids.

In one aspect of this embodiment, the method of solubilizing fatty acid particles in a formulation can comprise adding human serum albumin to a formulation capable of forming fatty acid particles, wherein the fatty acid particles can comprise free fatty acids and wherein a ratio of molecules of free fatty acid to molecules of human serum albumin can be about 6:1 to about 1:1.

In one aspect of this embodiment, the method of solubilizing fatty acid particles in a formulation can comprise adding human serum albumin to a formulation capable of forming fatty acid particles, wherein the fatty acid particles can comprise free fatty acids selected from the group consisting of oleic acid, palmitic acid, stearic acid, myristic acid, lauric acid, and combinations thereof.

In one aspect of this embodiment, the method of solubilizing fatty acid particles in a formulation can comprise adding at least about 5.5 mg/mL human serum albumin to a formulation capable of forming fatty acid particles.

In one aspect of this embodiment, the method of solubilizing fatty acid particles in a formulation can comprise adding human serum albumin to a formulation capable of forming fatty acid particles, wherein the formulation can be a parenteral formulation.

In one aspect of this embodiment, the method of solubilizing fatty acid particles in a formulation can comprise adding human serum albumin to a formulation capable of forming fatty acid particles, wherein the fatty acid particles are visible or sub-visible particles.

In one aspect of this embodiment, the method of solubilizing fatty acid particles in a formulation can comprise adding human serum albumin to a formulation capable of forming fatty acid particles, wherein the fatty acid particles are detectable by Raman spectroscopy.

This disclosure, at least in part, provides a formulation comprising (i) an active pharmaceutical agent and (ii) human serum albumin.

In one exemplary embodiment, the formulation can comprise (i) an active pharmaceutical agent, (ii) human serum albumin, and (iii) a polysorbate.

In one aspect of this embodiment, the formulation can comprise (i) an antibody, (ii) human serum albumin, and (iii) a polysorbate.

In one aspect of this embodiment, the formulation can comprise (i) an active pharmaceutical agent, (ii) human serum albumin, and (iii) a polysorbate selected from the group consisting of polysorbate 20, polysorbate 40, polysorbate 60, polysorbate 80, or combinations thereof.

In one aspect of this embodiment, the formulation can comprise (i) an antibody, (ii) human serum albumin, and (iii) a polysorbate, wherein the formulation can be administered by parenteral route.

In one aspect of this embodiment, the formulation can comprise (i) an antibody, (ii) human serum albumin, (iii) a polysorbate, and (iv) a lipase enzyme.

In one aspect of this embodiment, the formulation can comprise (i) an active pharmaceutical agent and (ii) at least about 5.5 mg/mL of human serum albumin.

In one aspect of this embodiment, the formulation can comprise (i) an active pharmaceutical agent, (ii) at least about 5.5 mg/mL of human serum albumin, and (iii) about 0.001% w/v to about 1% w/v polysorbate.

In one aspect of this embodiment, the formulation can comprise (i) an active pharmaceutical agent, (ii) human serum albumin, and (iii) a polysorbate, wherein the formulation can further comprise fatty acid particles having free fatty acids and wherein a ratio of molecules of the free fatty acid to molecules of the human serum albumin can be about 6:1 to about 1:1.

In one aspect of this embodiment, the formulation can comprise (i) an antibody, (ii) human serum albumin, and (iii) a polysorbate, wherein the polysorbate can degrade to form fatty acid particles.

In one aspect of this embodiment, the formulation can comprise (i) an antibody, (ii) human serum albumin, (iii) a polysorbate, and (iv) a lipase enzyme, wherein the lipase enzyme can hydrolyze the polysorbate to form fatty acid particles.

In one aspect of this embodiment, the formulation can comprise (i) an antibody, (ii) human serum albumin, and (iii) a polysorbate, wherein the formulation can further comprise fatty acid particles.

In one aspect of this embodiment, the formulation can comprise (i) an antibody, (ii) human serum albumin, and (iii) a polysorbate, wherein the formulation can further comprise fatty acid particles which include free fatty acids.

In one aspect of this embodiment, the formulation can comprise (i) an antibody, (ii) human serum albumin, and (iii) a polysorbate, wherein the formulation can further comprise fatty acid particles which include aliphatic fatty acids with about six to about twenty two carbons.

In one aspect of this embodiment, the formulation can comprise (i) an antibody, (ii) human serum albumin, and (iii) a polysorbate, wherein the formulation can further comprise fatty acid particles which include oleic acid.

In one aspect of this embodiment, the formulation can comprise (i) an antibody, (ii) human serum albumin, and (iii) a polysorbate, wherein the formulation can further comprise fatty acid particles which include free fatty acids selected from oleic acid, palmitic acid, stearic acid, myristic acid, lauric acid, and combinations thereof.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

DETAILED DESCRIPTION

Figure 1:
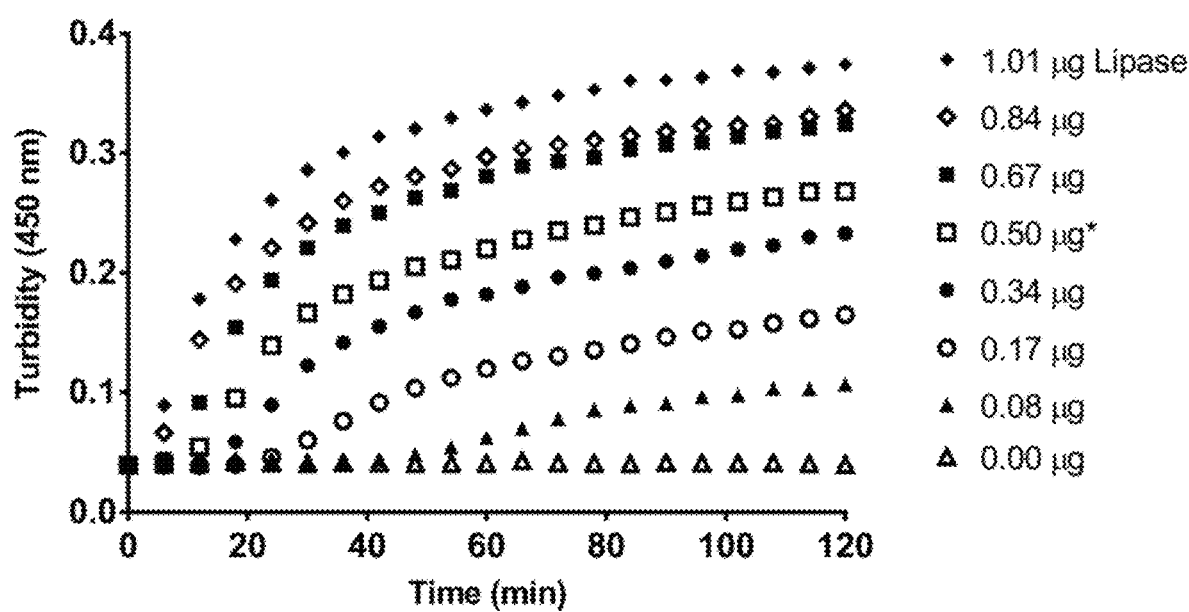
FIG. 1 shows a plot of absorbance at 450 nm as a function of time for lipase concentration to evaluate the ability of *Chromobacterium viscosum* lipase to generate fatty acid particles by promoting PS80 degradation, according to an exemplary embodiment.
Figure 2:
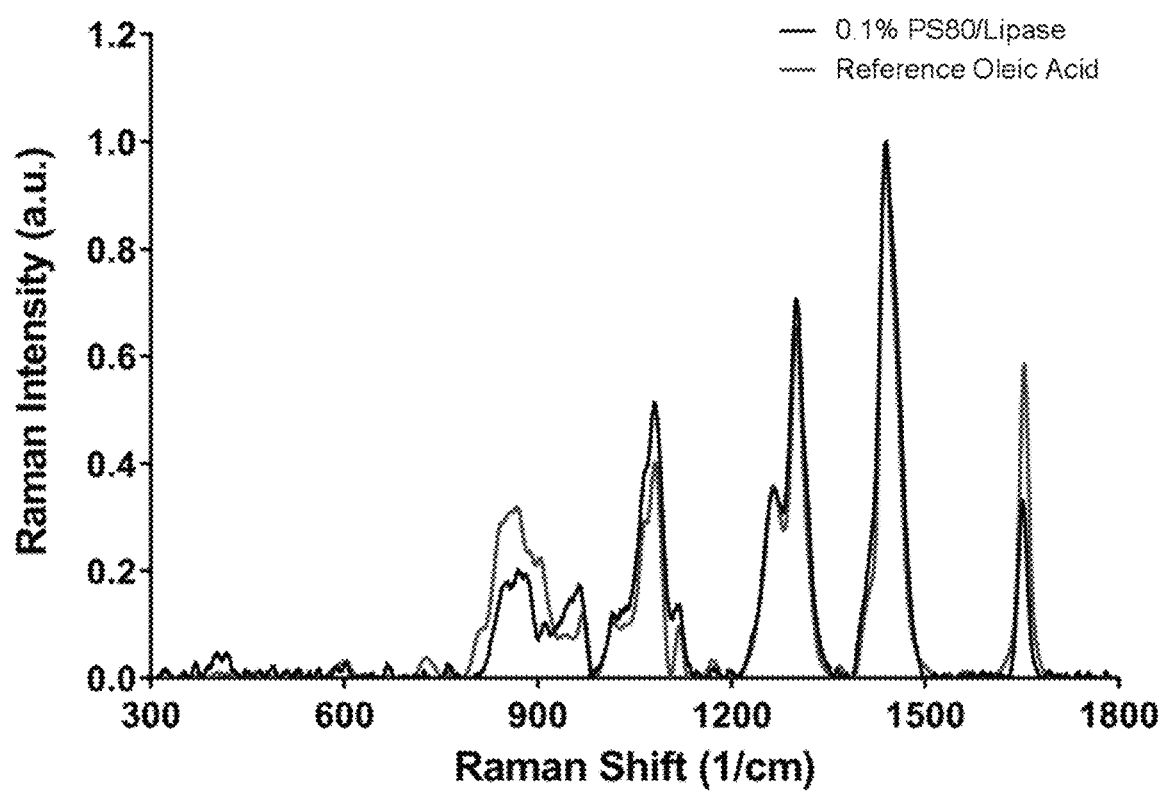
FIG. 2 shows the plot of Raman intensity (a.u.) as a function of Raman shift (1/cm) to identify the composition of particles attributed to fatty acids which were prepared according to an exemplary embodiment.

Among drug products, protein-based biotherapeutics are an important class of drugs that offer a high level of selectivity, potency, and efficacy, as evidenced by the considerable increase in clinical trials with monoclonal antibodies (mAbs) over the past several years. Bringing a protein-based biotherapeutic to the clinic can be a multiyear undertaking requiring coordinated efforts throughout various research and development disciplines, including discovery, process and formulation development, analytical characterization, and pre-clinical toxicology and pharmacology. One critical aspect for a clinically and commercially viable biotherapeutic is stability of the drug product in terms of the manufacturing process as well as shelf-life. Similar to many purified proteins, the native conformational stability of mAbs is relatively marginal, typically on the order of 20-25 kcal/mol (Kristi L. Lazar, Thomas W. Patapoff & Vikas K. Sharma, *Cold denaturation of monoclonal antibodies*, 2 mAbs 42-52 (2010)). This often necessitates appropriate steps to help increase mAb physical and chemical stability throughout the different solution conditions and environments necessary for manufacturing and storage with minimal impact on product quality, including identifying molecules with greater inherent stability, protein engineering, and formulation development. Formulation development seeks to identify solution conditions and additives or excipients that increase mAb stability and reduce the occurrence of chemical or physical changes that often result in aggregation and may subsequently lead to an increase in sub-visible or visible particles.

Visible and sub-visible particles, particularly in formulated drug products, have been the focus of debate and investigation within the pharmaceutical industry for several years and can pose a quality concern. Consisting of synthetic or biological materials and originating from various sources, particles raise the potential for immunogenic effects in patients (S. Bukofzer et al., *Industry Perspective on the Medical Risk of Visible Particles in Injectable Drug Products*, 69 PDA JOURNAL OF PHARMACEUTICAL SCIENCE AND TECHNOLOGY 123-139 (2015); S. E. Langille, *Particulate Matter in Injectable Drug Products*, 67 PDA JOURNAL OF PHARMACEUTICAL SCIENCE AND TECHNOLOGY 186-200 (2013)) and may have different effects on the drug product. There could be several causes for the formation of visible and sub-visible particles in a formulation, which can include proteinaceous particles and non-proteinaceous particles. Such particles can lead to increasing concerns about the potential immunogenicity. Even though the United States Pharmacopeia (USP) and the European Pharmacopoeia (Ph. Eur.) currently define concentration limits in parenteral solutions only for particles larger than 10 μm, regulatory authorities increasingly expect quantitative characterization of micron particles from 1 to 10 μm and qualitative characterization of submicron particles from 100 nm to 1000 nm already in early stages of the development phase (USP <788>. In: The United States Pharmacopoeia, National Formulary. 2009; Ph. Eur. 2.9.19).

Visible and sub-visible particles in drug formulations can be related to free fatty acid content and subsequent fatty acid particle formation. Free fatty acids and related fatty acid particle formation can occur in protein formulations comprising polysorbates. Over seventy percent of marketed monoclonal antibody therapeutics contain between 0.001% and 0.1% polysorbate to protect the protein against interfacial stresses, such as adsorption and aggregation. Many preparations of polysorbates contain a mixture of various fatty acid chains; for example, polysorbate 80 contains oleic, palmitic, myristic and stearic fatty acids, with the monooleate fraction making up approximately 58% of the polydisperse mixture (Nitin Dixit et al., *Residual Host Cell Protein Promotes Polysorbate* 20 *Degradation in a Sulfatase Drug Product Leading to Free Fatty Acid Particles*, 105 JOURNAL OF PHARMACEUTICAL SCIENCES 1657-1666 (2016)). Polysorbates are susceptible to auto-oxidation in a pH- and temperature-dependent manner, and additionally, exposure to UV light can also produce instability (Ravuri S. k. Kishore et al., *Degradation of Polysorbates 20 and 80: Studies on Thermal Autoxidation and Hydrolysis*, 100 JOURNAL OF PHARMACEUTICAL SCIENCES 721-731 (2011)), resulting in free fatty acids in solution along with the sorbitan head group. Thus, polysorbates can contribute to particle formation due to auto-oxidation and hydrolysis, which results in free fatty acids and subsequent fatty acid particle formation. Hydrolysis of polysorbate by various host cell proteins, such as phospholipase B-like 2 (PLBL2) and lipoprotein lipase (Josephine Chiu et al., *Knockout of a difficult-to-remove CHO host cell protein, lipoprotein lipase, for improved polysorbate stability in monoclonal antibody formulations*, 114 BIOTECHNOLOGY AND BIOENGINEERING 1006-1015 (2016)), can give rise to free fatty acids under certain conditions (Nitin Dixit et al., *Residual Host Cell Protein Promotes Polysorbate* 20 *Degradation in a Sulfatase Drug Product Leading to Free Fatty Acid Particles*, 105 JOURNAL OF PHARMACEUTICAL SCIENCES 1657-1666 (2016)). These free fatty acids and similarly the long chain fatty acids (stearate, oleate, palmitate, among others) that result from degradation of PS20 precipitate due to low solubility (Nidhi Doshi, Barthélemy Demeule & Sandeep Yadav, *Understanding Particle Formation: Solubility of Free Fatty Acids as Polysorbate* 20 *Degradation Byproducts in Therapeutic Monoclonal Antibody Formulations*, 12 MOLECULAR PHARMACEUTICS 3792-3804 (2015); Steven R. Labrenz, *Ester Hydrolysis of Polysorbate* 80 *in mAb Drug Product: Evidence in Support of the Hypothesized Risk After the Observation of Visible Particulate in mAb Formulations*, 103 JOURNAL OF PHARMACEUTICAL SCIENCES 2268-2277 (2014)), which in the current model potentially can lead to fatty acid particle formation in drug.

Several reports have detailed the presence of visible and sub-visible particles in drug products containing either polysorbate 20 or polysorbate 80 (Xiaolin Cao et al., *Free Fatty Acid Particles in Protein Formulations, Part* 1: *Microspectroscopic Identification*, 104 JOURNAL OF PHARMACEUTICAL SCIENCES 433-446 (2015); Christine C. Siska et al., *Free Fatty Acid Particles in Protein Formulations, Part* 2: *Contribution of Polysorbate Raw Material*, 104 JOURNAL OF PHARMACEUTICAL SCIENCES 447-456 (2015); Nidhi Doshi, Barthélemy Demeule & Sandeep Yadav, *Understanding Particle Formation: Solubility of Free Fatty Acids as Polysorbate* 20 *Degradation Byproducts in Therapeutic Monoclonal Antibody Formulations*, 12 MOLECULAR PHARMACEUTICS 3792-3804 (2015); Nitin Dixit et al., *Residual Host Cell Protein Promotes Polysorbate* 20 *Degradation in a Sulfatase Drug Product Leading to Free Fatty Acid Particles*, 105 JOURNAL OF PHARMACEUTICAL SCIENCES 1657-1666 (2016); Anthony Tomlinson et al., *Polysorbate* 20 *Degradation in Biopharmaceutical Formulations: Quantification of Free Fatty Acids, Characterization of Particulates, and Insights into the Degradation Mechanism*, 12 MOLECULAR PHARMACEUTICS 3805-3815 (2015); Troii Hall et al., *Polysorbates 20 and 80 Degradation by Group XV Lysosomal Phospholipase A 2 Isomer X*1 *in Monoclonal Antibody Formulations*, 105 JOURNAL OF PHARMACEUTICAL SCIENCES 1633-1642 (2016)). The particles characterized by spectroscopic methods and shown to be composed of fatty acids (Nidhi Doshi, Barthélemy Demeule & Sandeep Yadav, *Understanding Particle Formation: Solubility of Free Fatty Acids as Polysorbate* 20 *Degradation Byproducts in Therapeutic Monoclonal Antibody Formulations*, 12 MOLECULAR PHARMACEUTICS 3792-3804 (2015); Anthony Tomlinson et al., *Polysorbate* 20 *Degradation in Biopharmaceutical Formulations: Quantification of Free Fatty Acids, Characterization of Particulates, and Insights into the Degradation Mechanism*, 12 MOLECULAR PHARMACEUTICS 3805-3815 (2015), pure protein (Xiaolin Cao et al., *Free Fatty Acid Particles in Protein Formulations, Part* 1: *Microspectroscopic Identification*, 104 JOURNAL OF PHARMACEUTICAL SCIENCES 433-446 (2015)), or a mixture of fatty acids and protein, suggested that polysorbate hydrolysis can be directly contributing to the appearance of particles in formulated drug products. Host cell proteins, specifically lipases are cited as a likely root cause (Nitin Dixit et al., *Residual Host Cell Protein Promotes Polysorbate* 20 *Degradation in a Sulfatase Drug Product Leading to Free Fatty Acid Particles*, 105 JOURNAL OF PHARMACEUTICAL SCIENCES 1657-1666 (2016)). Thus, although under the current US Pharmacopeia (USP) standard for residual host cell protein is <100 ppm (Catalin Doneanu et al., *Analysis of host-cell proteins in biotherapeutic proteins by comprehensive online two-dimensional liquid chromatography/mass spectrometry*, 4 MABS 24-44 (2012)), the presence of minute levels of host cell lipases may lead to polysorbate hydrolysis, resulting in the release of free long-chain fatty acids. Furthermore, the criteria for particle content set forth by the USP sets limits at 6000 particles/container exceeding 10 µM in size and at 600 particles/container exceeding 25 µM in size (USP General Chapter 788, Particulate Matter in Injections), suggesting the presence of host cell lipases could potentially impact shelf life (S. Bukofzer et al., *Industry Perspective on the Medical Risk of Visible Particles in Injectable Drug Products*, 69 PDA JOURNAL OF PHARMACEUTICAL SCIENCE AND TECHNOLOGY 123-139 (2015)).

The overall homogeneity of polysorbate preparations as well as the inherent long-term stability of polysorbates can introduce issues related to free fatty acid content. Although the safety and efficacy of drug products containing fatty acid particles has not been fully evaluated, it is clearly advantageous to avoid the potential for quality concerns. While it remains unclear whether fatty acid particles produce an immunogenic response in patients, particulates in drug products, in general, are considered undesirable.

In absence of known methods to mitigate the formation of fatty acid particles or rapidly and completely solubilize pre-formed particles, effective and efficient methods and formulations were developed as disclosed herein. An experimental system to rapidly generate fatty acid particles and a novel use for human serum albumin in the context of biotherapeutic formulations is also disclosed.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

Since the presence of fatty acid particles in biotherapeutics can be a substantial concern throughout the industry companies, from companies to regulators to providers and patients, methods to prevent and/or reduce formation of such fatty acid-particles and formulations that can have reduced level of such fatty acid particles and/or prevent formation of such fatty acid particles is important in pharmaceutical drug development.

In some exemplary embodiments, the disclosure provides a formulation with a reduced level of fatty acid particles and/or capable of preventing formation of such fatty acid particles, comprising an active pharmaceutical agent.

As used herein, the term "formulation" refers to an active pharmaceutical agent that is formulated together with one or more pharmaceutically acceptable vehicles.

As used herein, the term "an active pharmaceutical agent" can include a biologically active component of a drug product. An active pharmaceutical agent can refer to any substance or combination of substances used in a drug product, intended to furnish pharmacological activity or to otherwise have direct effect in the diagnosis, cure, mitigation, treatment or prevention of disease, or to have direct effect in restoring, correcting or modifying physiological functions in animals. Non-limiting methods to prepare an active pharmaceutical agent can include using fermentation process, recombinant DNA, isolation and recovery from natural resources, chemical synthesis, or combinations thereof.

In some exemplary embodiments, the active pharmaceutical agent can be a protein.

As used herein, the term "protein" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. An another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Darius Ghaderi et al., *Production platforms for biotherapeutic glycoproteins. Occurrence, impact, and challenges of non-human sialylation*, 28 BIOTECHNOLOGY AND GENETIC ENGINEERING REVIEWS 147-176 (2012)). In some embodiments, proteins comprise modifications, adducts, and other covalently linked moieties. Those modifications, adducts and moieties include for example avidin, streptavidin, biotin, glycans (e.g., N-acetyl-galactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein can be an antibody, a bispecific antibody, a multispecific antibody, antibody fragment, monoclonal antibody, or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment contains sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain.

A typical bispecific antibody has two heavy chains each having three heavy chain CDRs, followed by a $C_H1$ domain, a hinge, a $C_H2$ domain, and a $C_H3$ domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats, such as, but not limited to triomab, knobs into holes IgG (kih IgG), crossMab, orth-Fab IgG, Dual-variable domains Ig (DVD-Ig), Two-in-one or dual action Fab (DAF), IgG-single-chain Fv (IgG-scFv), or κλ-bodies. The non-IgG-like different formats include Tandem scFvs, Diabody format, Single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang & Mingju Hao, *Bispecific antibodies and their applications*, 8 JOURNAL OF HEMATOLOGY & ONCOLOGY 130; Dafne Müller & Roland E. Kontermann, *Bispecific Antibodies*, HANDBOOK OF THERAPEUTIC ANTIBODIES 265-310 (2014)).

The methods of producing BsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated by reference: U.S. Ser. No. 12/823,838, filed Jun. 25, 2010; U.S. Ser. No. 13/488,628, filed Jun. 5, 2012; U.S. Ser. No. 14/031,075, filed Sep. 19, 2013; U.S. Ser. No. 14/808,171, filed Jul. 24, 2015; U.S. Ser. No. 15/713,574, filed Sep. 22, 2017; U.S. Ser. No. 15/713,569, field Sep. 22, 2017; U.S. Ser. No. 15/386,453, filed Dec. 21, 2016; U.S. Ser. No. 15/386,443, filed Dec. 21, 2016; U.S. Ser. No. 15/22,343 filed Jul. 29, 2016; and U.S. Ser. No. 15/814,095, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method.

As used herein "multispecific antibody" or "Mab" refers to an antibody with binding specificities for at least two different antigens. While such molecules normally will only bind two antigens (i.e. bispecific antibodies, BsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

In some exemplary embodiments, the formulation can comprise an active pharmaceutical agent, wherein the active pharmaceutical agent can be a small-molecule. As used herein, the term "small-molecule" can refer to low molecular chemical compounds with molecular weight of less than 1500 kDa.

In some exemplary embodiments, the formulation can be a protein formulation.

As used herein, the term "protein formulation" refers to a therapeutic protein that can be formulated together with one or more pharmaceutically acceptable vehicles. In some embodiments, the therapeutic protein can be present in a unit dose amount appropriate for administration in a therapeutic regimen.

In some other embodiments, the formulation can further comprise excipients including, but not limited to buffering agents, bulking agents, tonicity modifiers, surfactants, solubilizing agents, and preservatives. Other additional excipients can also be selected based on function and compatibility with the formulations may be found, for example in Remington: The Science and Practice of Pharmacy. Nineteenth Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999), herein incorporated by reference in their entirety.

In some exemplary embodiments, the formulation can be stable.

The stability of a formulation can comprise evaluating the chemical stability, physical stability or functional stability of the active pharmaceutical agent. The formulations of the present invention typically exhibit high levels of stability of the active pharmaceutical agent.

In terms of protein formulations, the term "stable," as used herein refers that the proteins within the formulations can retain an acceptable degree of chemical structure or biological function after storage under exemplary conditions defined herein. A formulation may be stable even though the protein contained therein does not maintain 100% of its chemical structure or biological function after storage for a defined amount of time. Under certain circumstances, maintenance of about 90%, about 95%, about 96%, about 97%, about 98% or about 99% of a protein's structure or function after storage for a defined amount of time may be regarded as "stable".

In some exemplary embodiments, the formulation can be used for the treatment, prevention and/or amelioration of a disease or disorder. Exemplary, non-limiting diseases and disorders that can be treated and/or prevented by the administration of the pharmaceutical formulations of the present invention include, infections; respiratory diseases; pain resulting from any condition associated with neurogenic, neuropathic or nociceptive pain; genetic disorder; congenital disorder; cancer; herpetiformis; chronic idiopathic urticarial; scleroderma, hypertrophic scarring; Whipple's Disease; benign prostate hyperplasia; lung disorders, such as mild, moderate or severe asthma, allergic reactions; Kawasaki disease, sickle cell disease; Churg-Strauss syndrome; Grave's disease; pre-eclampsia; Sjogren's syndrome; autoimmune lymphoproliferative syndrome; autoimmune hemolytic anemia; Barrett's esophagus; autoimmune uveitis; tuberculosis; nephrosis; arthritis, including chronic rheumatoid arthritis; inflammatory bowel diseases, including Crohn's disease and ulcerative colitis; systemic lupus erythematosus; inflammatory diseases; HIV infection; AIDS; LDL apheresis; disorders due to PCSK9-activating mutations (gain of function mutations, "GOF"), disorders due to heterozygous Familial Hypercholesterolemia (heFH); primary hypercholesterolemia; dyslipidemia; cholestatic liver diseases; nephrotic syndrome; hypothyroidism; obesity; atherosclerosis; cardiovascular diseases; neurodegenerative diseases; neonatal Onset Multisystem Inflammatory Disorder (NOM ID/CINCA); Muckle-Wells Syndrome (MWS); Familial Cold Autoinflammatory Syndrome (FCAS); familial mediterranean fever (FMF); tumor necrosis factor receptor-associated periodic fever syndrome (TRAPS); systemic onset juvenile idiopathic arthritis (Still's Disease); diabetes mellitus type 1 and type 2; auto-immune diseases; motor neuron disease; eye diseases; sexually transmitted diseases; tuberculosis; disease or condition which is ameliorated, inhibited, or reduced by a VEGF antagonist; disease or condition which is ameliorated, inhibited, or reduced by a PD-1 inhibitor; disease or condition which is ameliorated, inhibited, or reduced by a Interleukin antibody; disease or condition which is ameliorated, inhibited, or reduced by a NGF antibody; disease or condition which is ameliorated, inhibited, or reduced by a PCSK9 antibody; disease or condition which is ameliorated, inhibited, or reduced by a ANGPTL antibody; disease or condition which is ameliorated, inhibited, or reduced by an activin antibody; disease or condition which is ameliorated, inhibited, or reduced by a GDF antibody; disease or condition which is ameliorated, inhibited, or reduced by a Fel d 1 antibody; disease or condition which is ameliorated, inhibited, or reduced by a CD antibody; disease or condition which is ameliorated, inhibited, or reduced by a C5 antibody or combinations thereof.

In some exemplary embodiments, the formulation can be administered to a patient. Administration may be via any route. Non-limiting routes of administration include oral, topical, or parenteral. Administration via certain parenteral routes may involve introducing the formulations of the present invention into the body of a patient through a needle or a catheter, propelled by a sterile syringe or some other mechanical device such as a continuous infusion system. A formulation provided by the present invention may be administered using a syringe, injector, pump, or any other device recognized in the art for parenteral administration. A formulation of the present invention may also be administered as an aerosol for absorption in the lung or nasal cavity. The formulations may also be administered for absorption through the mucus membranes, such as in buccal administration.

In some exemplary embodiments, the human serum albumin can prevent formation of fatty acid particles. In some exemplary embodiments, the human serum albumin can solubilize pre-formed fatty acid particles. As used herein, "human serum albumin" or "HSA" can include the monomeric protein synthesized in the liver. It can be the primary macromolecular constituent of serum with a concentration up to 50 g/L and is in constant flux between intravascular and extravascular space (Angelica M. Merlot, Danuta S. Kalinowski & Des R. Richardson, *Unraveling the mysteries of serum albumin—"more than just a serum protein,* 5 FRONTIERS IN PHYSIOLOGY (2014)). Among various biological activities, HSA can transport of low solubility molecules, including fatty acids, throughout the body (Maja Thim Larsen et al., *Albumin-based drug delivery: harnessing nature to cure disease,* 4 MOLECULAR AND CELLULAR THERAPIES (2016)). HSA can contain nine distinct fatty acid binding sites, three high affinity, one medium affinity, and five low affinity sites (Eileen S. Krenzel, Zhongjing Chen & James A. Hamilton, *Correction to Correspondence of Fatty Acid and Drug Binding Sites on Human Serum Albumin: A Two-Dimensional Nuclear Magnetic Resonance Study,* 52 BIOCHEMISTRY 2382-2382 (2013)).

In some exemplary embodiments, the formulation can further comprise polysorbate.

As used herein, "polysorbate" refers to a common excipient used in formulation development to protect antibodies against various physical stresses such as agitation, freeze-thaw processes, and air/water interfaces (Emily Ha, Wei Wang & Y. John Wang, *Peroxide formation in polysorbate 80 and protein stability*, 91 JOURNAL OF PHARMACEUTICAL SCIENCES 2252-2264 (2002); Bruce A. Kerwin, *Polysorbates 20 and 80 Used in the Formulation of Protein Biotherapeutics: Structure and Degradation Pathways*, 97 JOURNAL OF PHARMACEUTICAL SCIENCES 2924-2935 (2008); Hanns-Christian Mahler et al., Adsorption Behavior of a Surfactant and a Monoclonal Antibody to Sterilizing-Grade Filters, 99 Journal of Pharmaceutical Sciences 2620-2627 (2010)). Polysorbate can include a non-ionic, amphipathic surfactant composed of fatty acid esters of polyoxyethylene-sorbitan such as polyoxyethylene sorbitan head group and either a saturated monolaurate side chain (polysorbate 20; PS20) or an unsaturated monooleate side chain (polysorbate 80; PS80). In some exemplary embodiments, the polysorbate can be present in the formulation in the range of 0.001% to 1% (weight/volume). Polysorbate can also contain a mixture of various fatty acid chains; for example, polysorbate 80 contains oleic, palmitic, myristic and stearic fatty acids, with the monooleate fraction making up approximately 58% of the polydisperse mixture (Nitin Dixit et al., *Residual Host Cell Protein Promotes Polysorbate 20 Degradation in a Sulfatase Drug Product Leading to Free Fatty Acid Particles*, 105 JOURNAL OF PHARMACEUTICAL SCIENCES 1657-1666 (2016)). Non-limiting examples of polysorbates include polysorbate-20, polysorbate-40, polysorbate-60, polysorbate-65, and polysorbate-80.

A polysorbate can be susceptible to auto-oxidation in a pH- and temperature-dependent manner, and additionally, exposure to UV light can also produce instability (Ravuri S. k. Kishore et al., *Degradation of Polysorbates 20 and 80: Studies on Thermal Autoxidation and Hydrolysis*, 100 JOURNAL OF PHARMACEUTICAL SCIENCES 721-731 (2011)), resulting in free fatty acids in solution along with the sorbitan head group. The free fatty acids resulting from polysorbate can include any aliphatic fatty acids with six to twenty carbons. Non-limiting examples of free fatty acids include oleic acid, palmitic acid, stearic acid, myristic acid, lauric acid, or combinations thereof.

In some exemplary embodiments, the fatty acid particles can be at least 5 µm in size. Further, these fatty acid particles can be classified according to their size as visible (>100 µm), sub-visible (<100 µm, which can be sub-divided into micron (1-100 µm) and submicron (100 nm-1000 nm)) and nanometer particles (<100 nm) (Linda Narhi, Jeremy Schmit & Deepak Sharma, *Classification of protein aggregates*, 101 JOURNAL OF PHARMACEUTICAL SCIENCES 493-498).

In some exemplary embodiments, the fatty acid particles can be visible particles. Visible particles can be determined by visual inspection.

In some exemplary embodiments, the fatty acid particles can be sub-visible particles. Subvisible particles can be monitored by the light blockage method according to United States Pharmacopeia (USP).

In some exemplary embodiments, the fatty acid particles can be formed from polysorbates. In some specific exemplary embodiments, the fatty acid particles can be formed from polysorbates in presence of a lipase enzyme. As used herein, "lipase" refers to an enzyme that can catalyze hydrolysis of fats. Lipases can be found across essentially all forms of life, from animals to plants to microbes. The mammalian lipase superfamily can be comprised of 7 different classes, differentiated by location and substrate specificity. Analysis of CHO-K1 mRNA has found 137 lipases and phospholipases, including variants (Benjamin G. Kremkow et al., *CHOgenome.org 2.0: Genome resources and website updates*, 10 BIOTECHNOLOGY JOURNAL 931-938 (2015)). A lipase specifically responsible for polysorbate degradation in purified biotherapeutic drug products has not been identified and it is likely that several will be found, suggesting an influence of the manufacturing process and the biotherapeutic itself. Several different lipases can be screened from mammalian, fungal, and bacterial origins available from commercial sources.

In some exemplary embodiments, the fatty acid particles can be detected by Raman Spectroscopy. As used herein, the term "Raman spectroscopy" refers to a spectroscopic method based on Raman scattering method. Raman Spectroscopy can provide a Raman spectrum, which can identify the presence and position of bands in the fingerprint region (2000 to 400 $cm^{-1}$) which enables the chemical identification of the analyzed material by comparison with a database of Raman spectra (C. V. Raman & K. S. Krishnan, *A New Type of Secondary Radiation*, 121 NATURE 501-502 (1928); Zai-Qing Wen, *Raman spectroscopy of protein pharmaceuticals*, 96 JOURNAL OF PHARMACEUTICAL SCIENCES 2861-2878 (2007)).

EXEMPLARY EMBODIMENTS

Embodiments disclosed herein provide compositions, methods, and systems for the rapid characterization of proteins in a sample.

As used herein, the terms "include," "includes," and "including," are meant to be non-limiting and are understood to mean "comprise," "comprises," and "comprising," respectively.

In some exemplary embodiments, the disclosure provides a method of preventing or reducing formation of fatty acid particles in a formulation comprising adding to the formulation an effective amount of human serum albumin.

In some exemplary embodiments, the disclosure provides a method of solubilizing fatty acid particles in a formulation comprising adding to the formulation an effective amount of human serum albumin.

In some exemplary embodiments, the disclosure provides a formulation comprising (i) an active pharmaceutical agent and (ii) human serum albumin.

In some specific exemplary embodiments, the active pharmaceutical ingredient can be a small-molecule. In some other specific exemplary embodiments, the active pharmaceutical ingredient can be a protein. In some exemplary embodiments, the active pharmaceutical ingredient can be a therapeutic protein.

In some exemplary embodiments, the formulation can comprise an antibody. In some specific exemplary embodiments, the formulation can comprise an antibody selected from a group consisting of monoclonal antibody, polyclonal antibody, antibody fragments, bispecific antibody, multispecific antibody, or combinations thereof.

In some exemplary embodiments, the formulation can comprise at least one active pharmaceutical agent. In some specific exemplary embodiments, the formulation can comprise two active pharmaceutical agents.

In some exemplary embodiments, the formulation can be used for treatment of a disease or a disorder.

In some exemplary embodiments, the formulation can be used for prevention of a disease or a disorder.

In some exemplary embodiments, the formulation can be administered to a patient.

In some specific exemplary embodiments, the formulation can be administered to a patient orally.

In some exemplary embodiments, the formulation can be administered to a patient via a parenteral route. In some specific embodiments, the formulation can be administered to a patient via an intravenous route. In some specific embodiments, the formulation can be administered to a patient via a subcutaneous route. In some specific embodiments, the formulation can be administered to a patient via an intramuscular route.

In some exemplary embodiments, the formulation can be a liquid formulation. In some exemplary embodiments, the amount of active pharmaceutical agent in the formulation can range from about 0.01 mg/mL to about 600 mg/mL. In some specific embodiments, the amount of active pharmaceutical agent in the formulation can be about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 5 mg/mL, about 80 mg/mL, about 85 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 225 mg/mL, about 250 mg/mL, about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL.

In some exemplary embodiments, the formulation can be capable of forming fatty acid particles. In some specific exemplary embodiments, the fatty acid particles can comprise free fatty acids. In some other specific exemplary embodiments, a ratio of molecules of free fatty acids to molecules of human serum albumin is about 6:1 to about 1:1. In some specific exemplary embodiments, the ratio of molecules of free fatty acids to molecules of human serum albumin is about 0.5:1, about 0.6:1, about 0.7:1, about 0.8:2, about 0.9:1, about 1:1, about 2:1, about 2:1, about 4:1, about 5:1, about 6:1, about 7:1, about 8:1, about 9:1, or about 10:1. In some specific exemplary embodiments, the fatty acid particles can comprise oleic acid.

In some specific exemplary embodiments, the fatty acid particles can comprise saturated straight chain aliphatic acids. In some other specific exemplary embodiments, the fatty acid particles can comprise saturated straight chain aliphatic acids with at most twenty carbon atoms. In some other specific exemplary embodiments, the free fatty acid can include of at least one fatty acid selected from ethanoic acid, propanoic acid, butanoic acid, pentanoic acid, hexanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, or combinations thereof.

In some specific exemplary embodiments, the fatty acid particles can comprise unsaturated straight chain aliphatic acids. In some specific exemplary embodiments, the fatty acid particles can comprise unsaturated straight chain aliphatic acids with at most twenty carbon atoms. In some exemplary embodiments, the free fatty acid particles can include stearidonic acid, linolelaidic acid, palmitoleic acid, vaccenic acid, paullinic acid, eladic acid, gondoic acid, oleic acid, palmitic acid, stearic acid, myristic acid, lauric acid, arachidic acid, palmitoleic acid, linoleic acid, arachidonic acid, and combinations thereof.

In some exemplary embodiments, the concentration of human serum albumin in the formulation can be at least about 2.5 mg/mL. In some specific exemplary embodiments, the concentration of human serum albumin in the formulation can be at least about 2.5 mg/mL, at least about 2.6 mg/mL, at least about 2.7 mg/mL, at least about 2.8 mg/mL, at least about 2.9 mg/mL, at least about 3.0 mg/mL, at least about 3.1 mg/mL, at least about 3.2 mg/mL, at least about 3.3 mg/mL, at least about 3.4 mg/mL, at least about 3.5 mg/mL, 3.6 mg/mL, at least about 3.7 mg/mL, at least about 3.8 mg/mL, at least about 3.9 mg/mL, at least about 4.0 mg/mL, at least about 4.1 mg/mL, at least about 4.2 mg/mL, at least about 4.3 mg/mL, at least about 4.4 mg/mL, at least about 4.5 mg/mL, 4.6 mg/mL, at least about 4.7 mg/mL, at least about 4.8 mg/mL, at least about 4.9 mg/mL, at least about 5.0 mg/mL, at least about 5.1 mg/mL, at least about 5.2 mg/mL, at least about 5.3 mg/mL, at least about 5.4 mg/mL, at least about 5.5 mg/mL, 5.6 mg/mL, at least about 5.7 mg/mL, at least about 5.8 mg/mL, at least about 5.9 mg/mL, at least about 6.0 mg/mL, at least about 6.1 mg/mL, at least about 6.2 mg/mL, at least about 6.3 mg/mL, at least about 6.4 mg/mL, at least about 6.5 mg/mL, 6.6 mg/mL, at least about 6.7 mg/mL, at least about 6.8 mg/mL, at least about 6.9 mg/mL, at least about 7.0 mg/mL, at least about 7.1 mg/mL, at least about 7.2 mg/mL, at least about 7.3 mg/mL, at least about 7.4 mg/mL, or at least about 7.5 mg/mL.

In some exemplary embodiments, the human serum albumin in the formulation can reduce the formation of fatty acid particles in a formulation.

In some exemplary embodiments, the human serum albumin in the formulation can solubilize fatty acid particles in a formulation.

In some exemplary embodiments, the human serum albumin in the formulation can bind free fatty acids generated by polysorbate degradation and sequester them, lowering the effective concentration in solution to levels below the critical micelle concentration.

In some exemplary embodiments, the human serum albumin in the formulation can serve as a fatty acid sink.

In some exemplary embodiments, the human serum albumin in the formulation can eliminate the appearance of visible/sub-visible fatty acid particles.

In some exemplary embodiments, the human serum albumin in the formulation can extend the shelf life of the formulation than the formulation without human serum albumin.

In some exemplary embodiments, the formulation can further comprise polysorbate. In some specific embodiments, the polysorbate can be selected from polysorbate 20, polysorbate 40, polysorbate 60, polysorbate 65, polysorbate 80, and combinations thereof. In some exemplary embodiments, the concentration of polysorbate in the formulation can be about 0.001% w/v to about 1% w/v. In some specific embodiments, the concentration of polysorbate in the formulation can be about 0.001% w/v, about 0.002% w/v, about 0.003% w/v, about 0.004% w/v, about 0.005% w/v, about 0.006% w/v, about 0.007% w/v, about 0.008% w/v, about 0.009% w/v, about 0.01% w/v, about 0.011% w/v, about 0.012% w/v, about 0.013% w/v, about 0.014% w/v, about 0.015% w/v, about 0.016% w/v, about 0.017% w/v, about 0.018% w/v, about 0.019% w/v, about 0.02% w/v, about 0.021% w/v, about 0.022% w/v, about 0.023% w/v, about 0.024% w/v, about 0.025% w/v, about 0.026% w/v, about 0.027% w/v, about 0.028% w/v, about 0.029% w/v, about 0.03% w/v, about 0.031% w/v, about 0.031% w/v, about 0.032% w/v, about 0.033% w/v, about 0.034% w/v, about 0.035% w/v, about 0.036% w/v, about 0.037% w/v, about 0.038% w/v, about 0.039% w/v, about 0.04% w/v, about 0.041% w/v, about 0.042% w/v, about 0.043% w/v, about 0.044% w/v, about 0.045% w/v, about 0.046% w/v, about 0.047% w/v, about 0.048% w/v, about 0.049% w/v, about 0.05% w/v, about 0.051% w/v, about 0.052% w/v, about 0.053% w/v, about 0.054% w/v, about 0.055% w/v, about 0.056% w/v, about 0.057% w/v, about 0.058% w/v, about 0.059% w/v, about 0.06% w/v, about 0.061% w/v, about 0.062% w/v, about 0.063% w/v, about 0.064% w/v, about 0.065% w/v, about 0.066% w/v, about 0.067% w/v, about 0.068% w/v, about 0.069% w/v, about 0.07% w/v, about 0.071% w/v, about 0.072% w/v, about 0.073% w/v, about 0.074% w/v, about 0.075% w/v, about 0.076% w/v, about 0.077% w/v, about 0.078% w/v, about 0.079% w/v, about 0.08% w/v, about 0.081% w/v, about 0.082% w/v, about 0.083% w/v, about 0.084% w/v, about 0.085% w/v, about 0.086% w/v, about 0.087% w/v, about 0.088% w/v, about 0.089% w/v, about 0.09% w/v, about 0.091% w/v, about 0.092% w/v, about 0.093% w/v, about 0.094% w/v, about 0.095% w/v, about 0.096% w/v, about 0.097% w/v, about 0.098% w/v, about 0.099% w/v, about 0.1% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.2% w/v, about 0.21% w/v, about 0.22% w/v, about 0.23% w/v, about 0.24% w/v, about 0.25% w/v, about 0.26% w/v, about 0.27% w/v, about 0.28% w/v, about 0.29% w/v, about 0.3% w/v, about 0.31% w/v, about 0.4% w/v, about 0.41% w/v, about 0.42% w/v, about 0.43% w/v, about 0.44% w/v, about 0.45% w/v, about 0.46% w/v, about 0.47% w/v, about 0.48% w/v, about 0.49% w/v, about 0.5% w/v, about 0.51% w/v, about 0.52% w/v, about 0.53% w/v, about 0.54% w/v, about 0.55% w/v, about 0.56% w/v, about 0.57% w/v, about 0.58% w/v, about 0.59% w/v, about 0.6% w/v, about 0.61% w/v, about 0.62% w/v, about 0.63% w/v, about 0.64% w/v, about 0.65% w/v, about 0.66% w/v, about 0.67% w/v, about 0.68% w/v, about 0.69% w/v, about 0.7% w/v, about 0.71% w/v, about 0.72% w/v, about 0.73% w/v, about 0.74% w/v, about 0.75% w/v, about 0.76% w/v, about 0.77% w/v, about 0.78% w/v, about 0.79% w/v, about 0.8% w/v, about 0.81% w/v, about 0.82% w/v, about 0.83% w/v, about 0.84% w/v, about 0.85% w/v, about 0.86% w/v, about 0.87% w/v, about 0.88% w/v, about 0.89% w/v, about 0.9% w/v, about 0.91% w/v, about 0.92% w/v, about 0.93% w/v, about 0.94% w/v, about 0.95% w/v, about 0.96% w/v, about 0.97% w/v, about 0.98% w/v, about 0.99% w/v, or about 1% w/v.

In some exemplary embodiments, the formulation can further comprise a lipase enzyme.

In some exemplary embodiments, the formulation can further comprise a polysorbate, and a lipase enzyme, wherein the lipase enzyme can hydrolyze the polysorbate to form fatty acid particles.

Various publications, including patents, patent applications, published patent applications, accession numbers, technical articles and scholarly articles are cited throughout the specification. Each of these cited references is incorporated by reference, in its entirety and for all purposes, herein.

The present invention will be more fully understood by reference to the following Examples. They should not, however, be construed as limiting the scope of the invention

EXAMPLES

Materials and Reagent Preparation.

All reactions were carried out in an aqueous buffered solution containing 25 mM Tris, pH 7.5, 100 mM KCl, 20 mM $CaCl_2$) (TKC buffer) unless otherwise indicated. *Chromobacterium viscosum* lipase was purchased from EMD Millipore (Billerica, Mass.); lyophilized fatty acid free Human Serum Albumin (FAF-HSA) and human serum were purchased from Sigma-Aldrich (St. Louis, Mo.). Super refined polysorbate 20 (PS20) and polysorbate 80 (PS80) were obtained from Croda (Edison, N.J.). For experiments with IgG, human lyophilized polyclonal IgG purchased from Sigma-Aldrich (St. Louis, Mo.) was reconstituted per manufacturer's recommendation with 150 mM NaCl and 35 mM Tris pH 8.0 and desalted on a Zeba spin desalting column (Thermo Fisher Scientific) equilibrated with 25 mM Tris, 100 mM KCl, pH 7.5

Purification of Reagents.

Lyophilized *C. viscosum* lipase was reconstituted in approximately 1 mL of TKC reaction buffer and purified over a Superdex Increase 200 10/300 SEC column equilibrated in the same buffer. Purified lipase fractions were pooled and the protein concentration (4.2 mg/mL) was determined with a Nanodrop One C spectrophotometer at $UV_{\lambda=280\ nm}$ using an extinction coefficient of 0.95. Aliquots were stored in 10% (v/v) glycerol at −20° C. FAF-HSA concentration was determined with a Nanodrop OneC at $UV_{\lambda=280\ nm}$ using an extinction coefficient of 0.531.

Particle Detection by Turbidity Measurement.

A plate-based assay was used to detect the presence of particles by monitoring absorbance at 450 nm over time, typically 2-4 hours. The assay detects particles larger than approximately 20 nm, based on fundamental principles of light scattering (assessment of turbidity). Purified lipase was added to TKC buffer containing 0.1% polysorbate 80 at final concentration ranging from 0.4 to 5 μg/mL. The absorbance was measured at 5 minute intervals with intermittent shaking on a Spectra Max 340 plate reader held at 25° C. Baseline values were established by measuring absorbance of 0.1% polysorbate 80 without addition of lipase. Instrument control, data acquisition, and analysis were performed using SoftMax Pro software (version 6.5).

Several different lipases from mammalian, fungal, and bacterial origins from commercial sources were screened. The selection of the bacterial lipase was largely based on the rapid polysorbate hydrolysis and subsequent particle formation, offering a distinct advantage for identifying conditions to control particle formation, which may take months to years in a biotherapeutic drug product setting. Additionally, the bacterial lipase was amenable to a wider range of solution conditions, which strongly influence particle formation. In particular, the presence of potassium to help neutralize the electrostatic repulsion of the acidic head groups, is essential.

Example 1. Hydrolysis of Polysorbate 80 by *Chromobacterium viscosum* Lipase in Particle Formation Formation of particles in solutions containing PS80 can occur due to hydrolysis by lipases (Nitin Dixit et al., *Residual Host Cell Protein Promotes Polysorbate* 20 *Degradation in a Sulfatase Drug Product Leading to Free Fatty Acid Particles,* 105 JOURNAL OF PHARMACEUTICAL SCIENCES 1657-1666 (2016)).

Particle formation is a multi-step process: first, lipase catalyzes hydrolysis of PS80 at the fatty acid ester bond to release a sorbitan ring and the fatty acid chain; second, multiple free fatty acids aggregate to form particles. In order to test activity of *Chromobacterium viscosum* lipase, 0.1% PS80 was incubated with various concentrations of lipase between 0.4 to 5 μg/mL and thabsorbance at 450 nm was monitored over several hours.

In order to detect the presence of particles in solution, sample turbidity was monitored with absorbance spectroscopy. Samples were incubated at 25° C. and absorbance at 450 nm was taken over the course of 120 minutes. Different concentration of lipase between 0 and 1 μg was used. The sample containing no lipase was used as control.

An increase in signal at 450 nm is indicative of an increase in solution turbidity, which is attributed to particle formation. FIG. 1 shows that increasing lipase concentration resulted in both an elevated final turbidity and a decrease in the time needed to observe the initial increase in a dose-dependent response. Further, the sample containing no lipase was used as control (open triangles) did not increase in turbidity over time and provided a baseline absorbance level.

Example 2. Identification of Composition of Particles Formed 2.1 Preparation of Particles.

Particles were prepared by incubating 2.5 μg/mL lipase with PS80 in TKC buffer at room temperature for 3 hours, followed by centrifugation. The supernatant was discarded and the pellet was washed with buffer one time and reconstituted by sonication. For particle generation in the presence of IgG, human polyclonal IgG was added to a final concentration of 7.5 mg/mL. Mechanically dispersed pellets were deposited on 5 μm polycarbonate membrane filters (RapID; Monmouth Junction, N.J.). Raman spectroscopy was performed on the particle using a RapID Single Particle Explorer with a 785 nm monochromatic laser at 100% intensity/10 second exposure time in the 50× objective to generate spectra specific to the sample.

2.2 Raman Spectroscopy.

Raman spectroscopy was employed to identify particle constituents following incubation of lipase with PS80. This method uses inelastic light scattering to generate an energy spectrum unique to each molecule, which is then compared to a reference library containing the fingerprints of various chemical structures. The Raman spectra of 156 out of 200 particles were identified to be highly similar to the spectrum of oleic acid (FIG. 2). The black trace as seen in FIG. 2 is the internal reference oleic acid. The peak at 1650 $cm^{-1}$ is directly proportional to the number of C═C bonds in a linear hydrocarbon chain and thus is a signature of the unsaturated oleic acid hydrocarbon chain. Other identified species included lauric acid and palmitic acid, both of which are also degradation products of polysorbate.

Example 3. Prevention of Particle Formation by HSA

HSA contains several high and low affinity binding sites for fatty acids and therefore has the potential to act as a fatty acid sink, which could inhibit particle formation upon polysorbate hydrolysis. To test the effectiveness of HSA in preventing particle formation, 0.1% PS80 was incubated with 0.5 μg lipase in the presence of increasing concentrations of FAF-HSA at 25° C. and the solution turbidity was monitored by measuring the absorbance at 450 nm for six hours.

FIG. 3 shows the graph plots absorbance at 450 nm as a function of time for various FAF-HSA concentrations. The sample without FAF-HSA (open diamonds) provides the upper limit for absorbance (~0.4 nm). As seen in FIG. 3, the effect of HSA on the appearance of particles was a dose dependent response wherein the error bars represent standard error from two replicates. The control sample contained no FAF-HSA and showed a final absorbance of approximately 0.4 OD after 6 hours. Addition of FAF-HSA resulted in both a decrease in the final absorbance (lower turbidity) as well as a temporal delay in the onset of turbidity in a concentration dependent manner. Notably, samples containing 7.5 mg/mL FAF-HSA did not show any appreciable absorbance over this time period. Similar results were obtained with PS20 in place of PS80 (data not shown).

Example 4. Partial Saturation of Fatty Acid Binding Sites Prevents HSA from Mitigating Particle Formation To further define the molecular mechanism by which HSA inhibits particle formation, measurement of turbidity changes in solutions containing HSA that had been pre-incubated with stearic acid in stoichiometric ratio with the three high affinity binding sites, was carried out. Although oleic acid would be a more direct comparison, the solubility of the mono-unsaturated fatty acid made it difficult minimizes transfer of free fatty acid to the samples; therefore, stearic acid, a saturated molecule with an equivalent number of hydrocarbons, was chosen as a comparable substitute.

HSA loaded with stearic acid (SA-HSA) was prepared by adding 70 mM pure stearic acid (Sigma) in ethanol to FAF-HSA in a 3:1 molar ratio, incubating at room temperature for 30-60 minutes at 25° C., then centrifuging at 22,000 rcf for 4 minutes to pellet un-bound steric acid, followed by addition of 0.5 mg lipase and 0.1% PS80, and absorbance at 450 nm was monitored for six hours.

The plot in FIG. 4 depicts absorbance at 450 nm as a function of time for various SA-HSA concentrations and the sample without SA-HSA (open circles) provides the upper limit for absorbance (~0.5) while the error bars represent standard error from three replicates.

Whereas FAF-HSA exhibited a dose-dependent decrease in turbidity with complete inhibition at 7.5 mg/mL, an increase in turbidity was detected in all samples containing SA-HSA, indicating that particle formation was not inhibited (FIG. 4). In addition, the time required for onset of turbidity was shorter compared to samples containing equivalent amounts of FAF-HSA (FIG. 3).

Example 5. Mitigation of Particle Formation in an Antibody Preparation without HSA Mitigation of particle formation appeared to be directly proportional to the concentration of HSA added to the polysorbate/lipase mixture; however, the possibility that any protein could non-specifically prevent particle formation remained. In order to determine if this effect is specific to HSA or could be a general property of any protein species, human polyclonal IgG, the second most abundant circulating serum protein (N. Leigh Anderson & Norman G. Anderson, *The Human Plasma Proteome: History, Character, and Diagnostic Prospects,* 1 Molecular & Cellular Proteomics 845-867 (2002) was substituted for HSA and the solutions were monitored for turbidity over time.

For experiments with IgG, human polyclonal IgG purchased from Sigma-Aldrich (St. Louis, Mo.) was reconstituted per manufacturer's recommendation with 150 mM NaCl and 35 mM Tris pH 8.0 and desalted on a Zeba spin desalting column (Thermo Fisher Scientific) equilibrated with 25 mM Tris, 100 mM KCl, and pH 7.5.

To test specificity of fatty acid particle mitigation to HSA, different concentrations of human polyclonal IgG were added to solution containing 0.5 µg lipase and 0.1% PS80 at 25° C. and absorbance at 450 nm was monitored for six hours.

A positive control sample with lipase and PS80 but without IgG (FIG. 5, open diamonds) was used to provide an upper limit for absorbance (~0.5). A sample with PS80 and 10 mg/mL IgG, but without lipase (red triangles) was used to provide a negative control which shows baseline absorbance at 450 nm.

Figure 5:
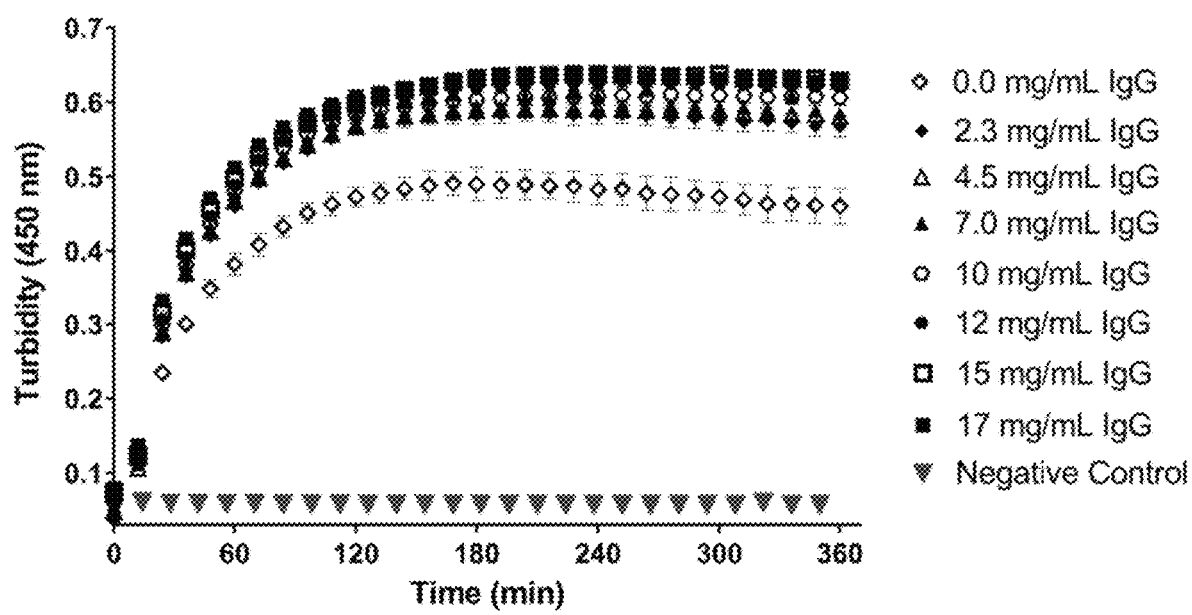
FIG. 5 shows a plot of absorbance at 450 nm as a function of time for various polyclonal IgG concentrations without the addition of HSA.

In contrast to the decrease in turbidity observed for samples containing FAF-HSA, all samples containing poly-IgG rapidly showed an increase in absorbance, indicating it does not prevent particle formation (FIG. 5). Surprisingly, the apparent level of turbidity showed a modest poly-IgG concentration-dependent increase compared to the positive control containing no IgG; however, it is difficult to determine if the increase in absorbance was caused by an increase in the number of particles or an increase in average particle size. Aggregation was not observed in the negative control (FIG. 5, red triangles).

Figure 6:
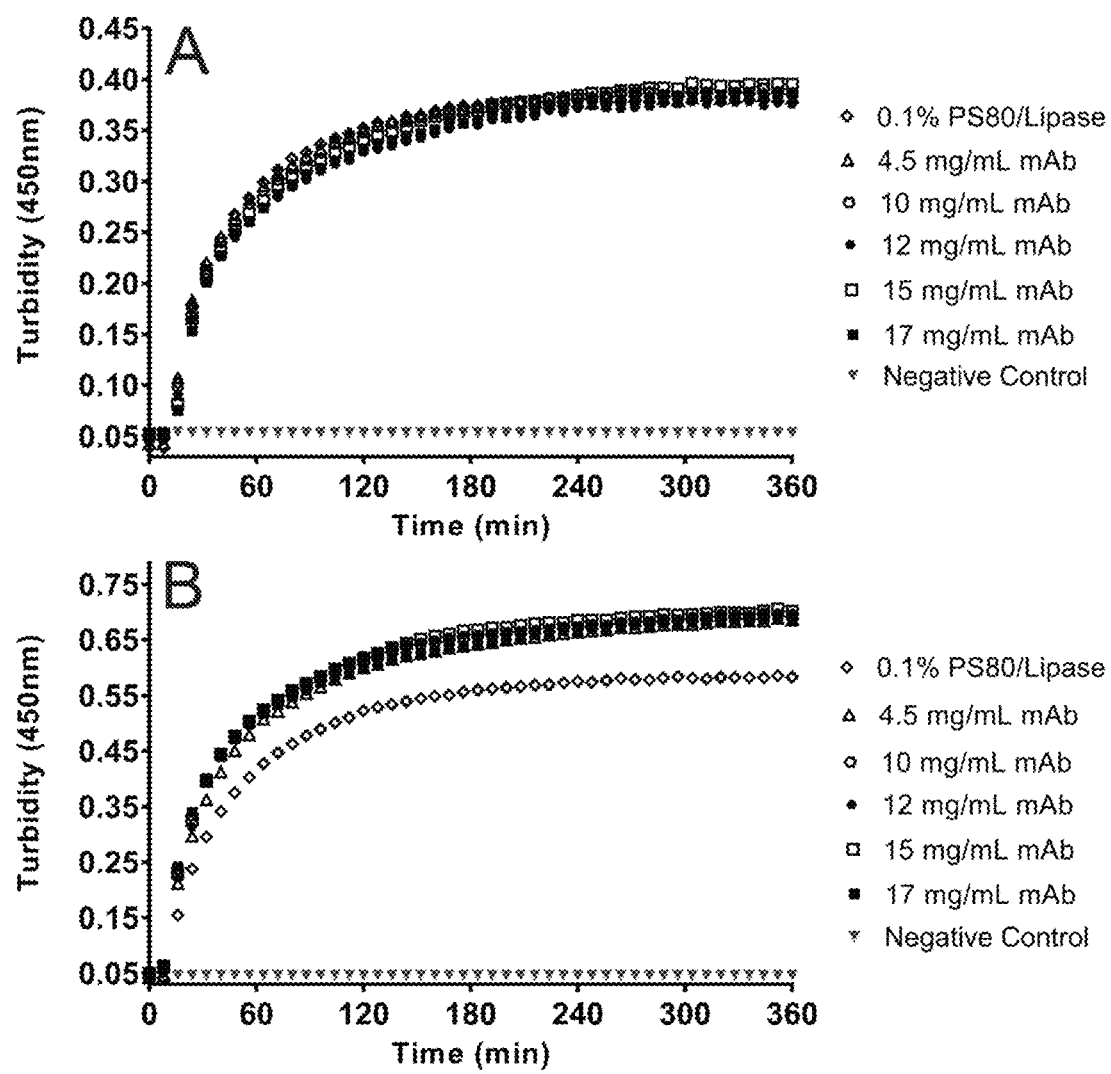
FIG. 6 shows a plot of absorbance at 450 nm as a function of time for formulations comprising a monoclonal antibody which is not lyophilized (panel A) and lyophilized (panel B).

The increase in turbidity can likely attributed to protein lyophilization. To determine if the increase in turbidity was due to the way that the protein was processed (i.e., lyophilized), a solution-state mAb in two ways was prepared; one that was unmodified from its purified solution state, and one that mimicked the manufacturer's lyophilization process used for the poly IgG preparation. The monoclonal antibody was lyophilized and reconstituted per the polyclonal IgG manufacturer's instructions to replicate processing, and then added to a solution containing 0.5 µg lipase and 0.1% PS80 at 25° C. and absorbance at 450 nm was monitored for six hours. Panel A of FIG. 6 shows a monoclonal antibody that has not been lyophilized. Panel B of FIG. 6 shows the same monoclonal antibody that has been lyophilized. The plots depict absorbance at 450 nm as a function of time for various monoclonal IgG concentrations. A positive control sample with lipase and PS80 but without IgG (open diamonds) provides the upper limit for absorbance (~0.55). A negative control sample with PS80 and 10 mg/mL IgG, but without lipase (red triangles), shows baseline absorbance at 450 nm. The lyophilized material showed a similar uptick to that of poly-IgG, demonstrating that this uptick was likely due to the lyophilization process.

Example 6. Mitigation of Particle Formation in an Antibody Preparation with HSA In-Vitro To evaluate whether HSA could mitigate particle formation in the presence of polyclonal IgG, assay with increasing concentrations of polyclonal IgG, a test with HSA, polyclonal IgG, lipase, and PS80 was performed.

4.5 mg/mL FAF-HSA and 7.5 mg/mL FAF-HSA were added to samples containing polyclonal IgG, 0.5 µg lipase, and 0.1% PS80 at 25° C., and absorbance at 450 nm was monitored for six hours.

Figure 7:
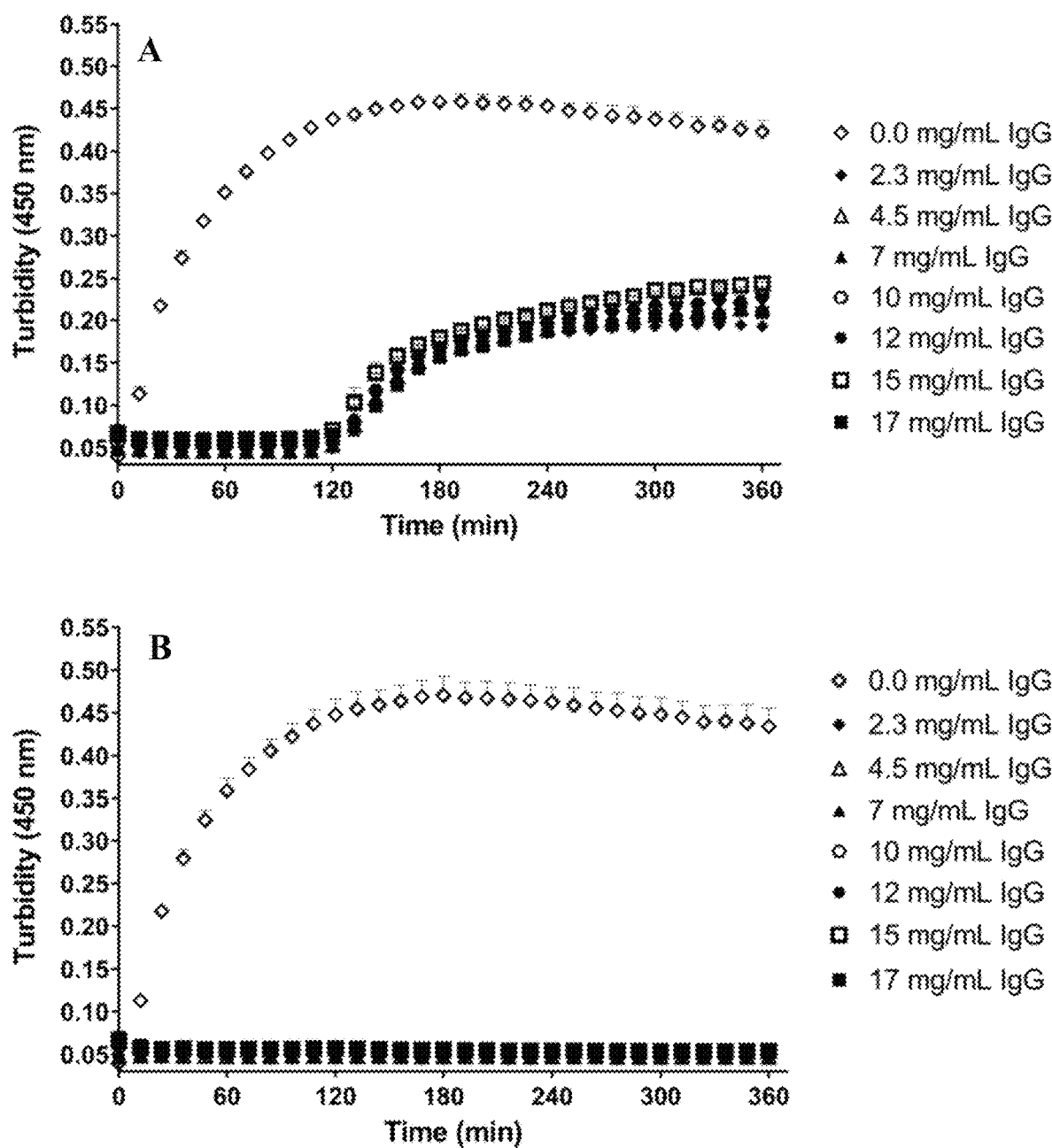
FIG. 7 shows a plot of absorbance at 450 nm as a function of time on addition of 4.5 mg/mL FAF-HSA (panel A) and 7.5 mg/mL FAF-HSA (panel B) to various polyclonal IgG concentrations according to an exemplary embodiment.

FIG. 7 depict the plots for absorbance at 450 nm as a function of time for addition of 4.5 mg/mL FAF-HSA and 7.5 mg/mL FAF-HSA to various polyclonal IgG concentrations. A positive control sample with lipase and PS80 but without IgG (open diamonds) provides the upper limit for absorbance (~0.5) and error bars represent standard error from two replicates.

Figure 3:
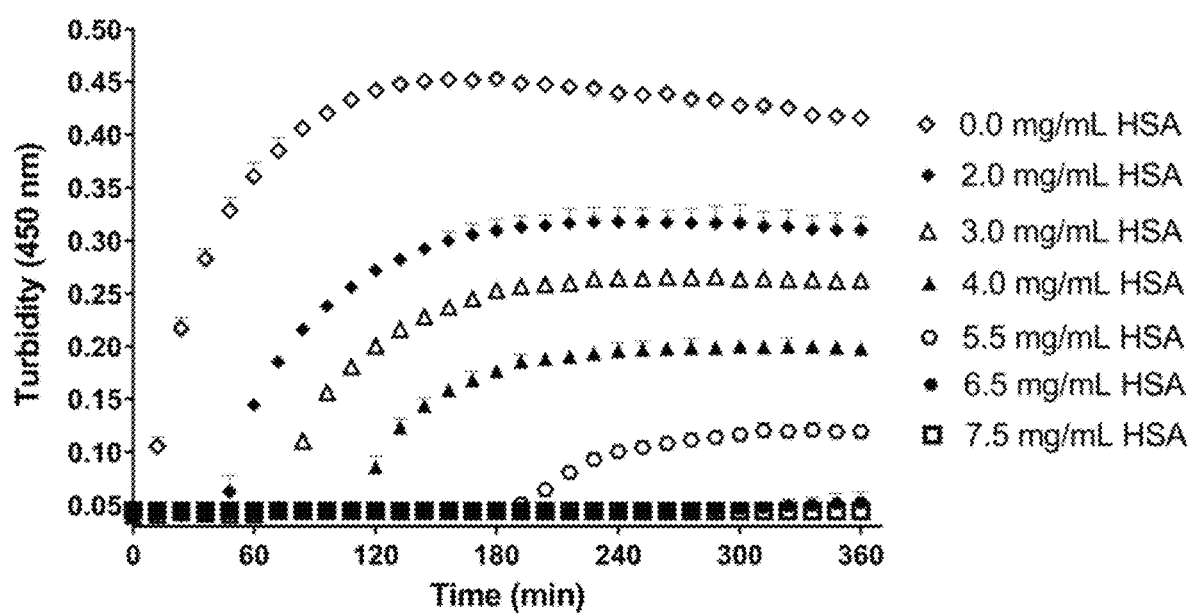
FIG. 3 shows the plot of absorbance at 450 nm as a function of time for various FAF-HSA concentrations added to polysorbate containing solution prepared according to an exemplary embodiment.
Figure 4:
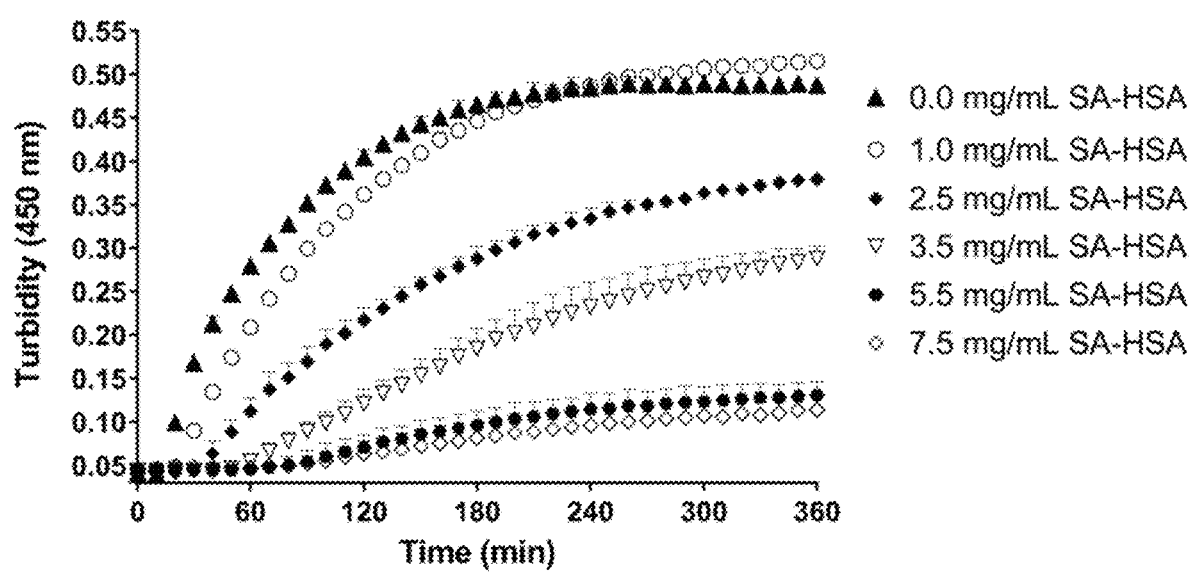
FIG. 4 shows the plot of absorbance at 450 nm as a function of time for various SA-HSA concentrations added to polysorbate containing solution prepared according to an exemplary embodiment.

Particle inhibition activity of HSA was similar to that observed in the absence of polyclonal IgG at (FIG. 3), indicating that HSA inhibits formation of particles even in the presence of another serum protein.

Example 7. Mitigation of Particle Formation in an Antibody Preparation with HSA In-Vivo The rapid lipase-mediated particle formation and detection assay described above demonstrated that HSA could prevent the formation of particles, in vitro. As a first step towards a more relevant in vivo setting, whether HSA could solubilize pre-existing particles was evaluated.

Figure 8:
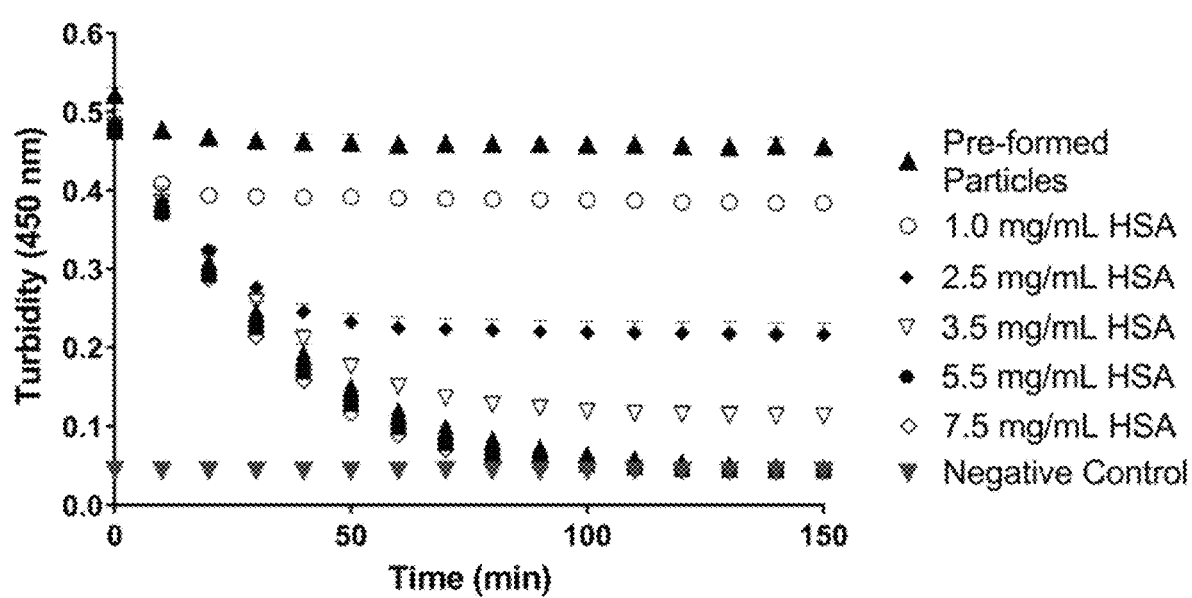
FIG. 8 shows a plot of absorbance at 450 nm as a function of time for various serum concentrations added to pre-formed fatty acid particles according to an exemplary embodiment.

To test the ability of HSA to solubilize pre-formed particles in solution, particles were prepared (See Materials and Methods) and diluted to obtain a maximum absorbance of ~0.5 OD. Pre-formed particles were incubated with FAF-HSA and absorbance at 450 nm was monitored for six hours as shown in FIG. 8 (data displayed to show 2.5 hours). A positive control sample with lipase and PS80 but without HSA (FIG. 8, closed triangles) provides the upper limit for absorbance (~0.5). A negative control sample with PS80 and 7.5 mg/mL HSA, but without lipase (FIG. 8, red triangles), shows baseline absorbance at 450 nm and the error bars represent standard error from three replicates.

Upon addition of FAF-HSA to solutions containing elevated levels of fatty acid particles, the solution turbidity rapidly decreased; however, not all concentrations of FAF-HSA achieved the baseline level (FIG. 8). The plateaus observed in HSA concentrations less than or equal to 3.5 mg/mL indicate that the pre-formed particles were not fully solubilized. HSA concentrations above 5.5 mg/mL were necessary to fully disrupt pre-formed particles, within the limits of the turbidity assay.

Example 8. Mitigation of Particle Formation in an Antibody Preparation with HSA In-Vivo with Human Serum Similar experiments as example 7 were also performed with human serum, which more closely represents physiological conditions. In particular, the albumin present in serum is bound with numerous different low solubility compounds.

Figure 9:
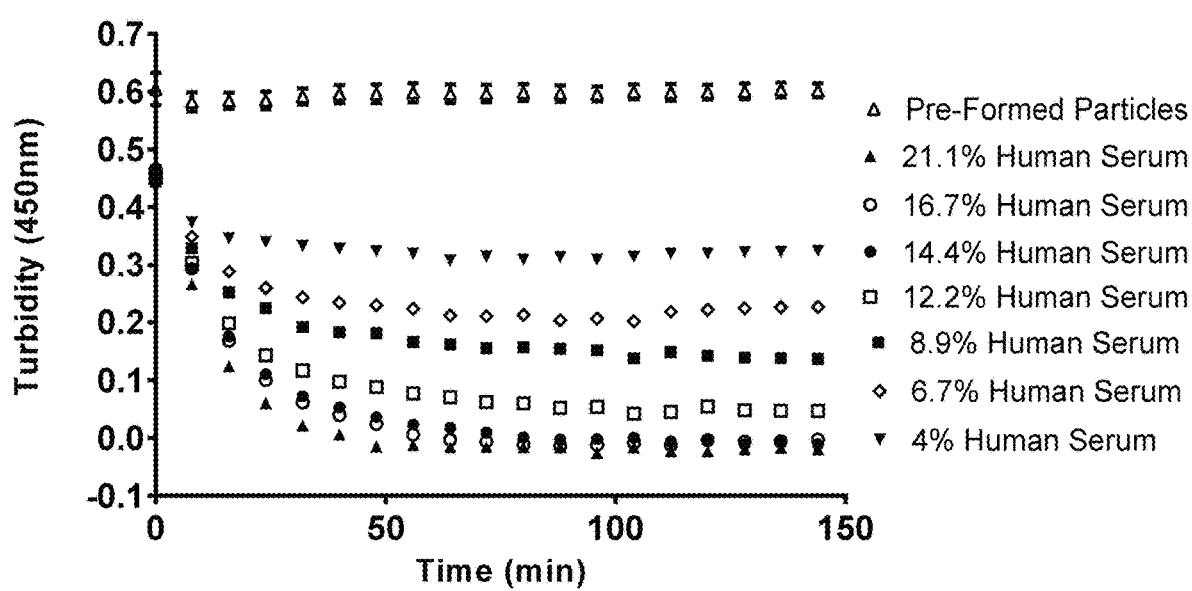
FIG. 9 shows a plot of absorbance at 450 nm as a function of time for formulations comprising human serum and pre-formed free fatty acid particles in solution.

Pre-formed particles were incubated with normal human serum, and the absorbance at 450 nm was monitored for six hours as shown in FIG. 9 (data to 2.5 hours shown as no further changes were observed). A positive control sample with lipase and PS80 but without serum (open triangles) provides the upper limit for absorbance (~0.6). A negative control sample with PS80 and 21% human serum, but without lipase was included (data not shown) and obtained an absorbance of 0.25 OD and the error bars represent standard error from three replicates. Due to the baseline absorbance of human serum, each concentration of serum was also analyzed without lipase, PS80, or particles and the results shown in FIG. 9 depict background subtracted signals.

While all samples containing serum exhibited a decrease in turbidity, only those with at least 14% serum were able to obtain a baseline indicative of essentially no particles within 1.5 hours. Assuming an upper limit of 50 mg/mL albumin in human serum, this equates to approximately 7.5 mg/mL albumin in line with the amount of FAF-HSA necessary to obtain a zero turbidity baseline.

Thus, a novel and potentially beneficial use for human serum albumin in the biopharmaceutical industry was discovered. HSA can mitigate fatty acid particle formation, indicating inclusion of HSA as an excipient may help extend the shelf-life of certain polysorbate-containing drug products. Importantly, HSA can also solubilize pre-existing particles in solution, suggesting that physiological concentrations of HSA may efficiently and effectively eliminate particles, if present, post-administration of a drug product.

What is claimed is:

1. A method of reducing formation of fatty acid particles in a formulation capable of forming fatty acid particles, comprising:
    (a) obtaining a formulation comprising an active pharmaceutical agent, a polysorbate, and at least one lipase, wherein said formulation is capable of forming fatty acid particles; and
    (b) adding to the formulation an effective amount of human serum albumin.

2. The method of claim 1, wherein the fatty acid particles comprise a free fatty acid selected from the group consisting of oleic acid, palmitic acid, stearic acid, myristic acid, lauric acid, and combinations thereof.

3. The method of claim 2, wherein a ratio of molecules of the free fatty acid to molecules of the human serum albumin in the formulation is about 6:1 to about 1:1.

4. The method of claim 1, wherein concentration of the human serum albumin in the formulation is at least about 5.5 mg/mL.

5. The method of claim 1, wherein the method is capable of reducing fatty acid particles that form visible or sub-visible particles.

6. The method of claim 1, wherein an effective amount of human serum albumin includes one mole of human serum albumin binding to at least a half mole of a free fatty acid contained in the fatty acid particles.

7. The method of claim 1, wherein the method is capable of reducing the formation of fatty acid particles at least 10 μm in size.

8. The method of claim 1, further comprising using Raman spectroscopy to detect the fatty acid particles.

9. The method of claim 1, wherein the polysorbate is selected from the group consisting of polysorbate 20, polysorbate 40, polysorbate 60, polysorbate 80, and a combination thereof.

10. A method of solubilizing fatty acid particles formed in a formulation, comprising:
    (a) obtaining a formulation comprising an active pharmaceutical agent, a polysorbate, and at least one lipase, wherein said formulation is capable of forming fatty acid particles; and
    (b) adding to the formulation an effective amount of human serum albumin.

* * * * *